US009945765B2

(12) United States Patent
White et al.

(10) Patent No.: US 9,945,765 B2
(45) Date of Patent: Apr. 17, 2018

(54) ENVIRONMENTAL SENSOR AND A METHOD FOR DETERMINING RELATIVE VAPOUR PRESSURE

(71) Applicant: Provenance Asset Group LLC, Essex, CT (US)

(72) Inventors: Richard White, Cambridgeshire (GB); Stefano Borini, Cambridge (GB)

(73) Assignee: Provenance Asset Group LLC, Essex, CT (US)

(*) Notice: Subject to any disclaimer, the term of this patent is extended or adjusted under 35 U.S.C. 154(b) by 37 days.

(21) Appl. No.: 14/905,384

(22) PCT Filed: Jun. 25, 2014

(86) PCT No.: PCT/FI2014/050513
§ 371 (c)(1),
(2) Date: Jan. 15, 2016

(87) PCT Pub. No.: WO2015/007947
PCT Pub. Date: Jan. 22, 2015

(65) Prior Publication Data
US 2016/0153882 A1    Jun. 2, 2016

(30) Foreign Application Priority Data
Jul. 16, 2013 (GB) .................................. 1312658.6

(51) Int. Cl.
*G01N 7/14* (2006.01)
*G01N 27/414* (2006.01)
(Continued)

(52) U.S. Cl.
CPC .............. *G01N 7/14* (2013.01); *G01L 9/0098* (2013.01); *G01N 27/4141* (2013.01); *G01N 27/02* (2013.01)

(58) Field of Classification Search
CPC ...... G01N 7/14; G01N 27/4141; G01N 27/02; G01L 9/0098
See application file for complete search history.

(56) References Cited

U.S. PATENT DOCUMENTS 5,004,700 A    4/1991   Webb et al.
5,563,341 A    10/1996  Fenner et al.
(Continued)

FOREIGN PATENT DOCUMENTS

EP    2239561 A1    10/2010
EP    2426487       3/2012
(Continued)

OTHER PUBLICATIONS

Office action received for corresponding Chinese Patent Application No. 201480050709.0, dated Apr. 28, 2017, 8 pages of office action and no page translation available.
(Continued)

*Primary Examiner* — Ryan Walsh
(74) *Attorney, Agent, or Firm* — Dinsmore & Shohl LLP

(57) ABSTRACT

An apparatus for use in determining the relative vapor pressure of a fluid in an environment in which the apparatus is located, the apparatus comprising a first layer (512) configured to enable a flow of charge carriers from a source electrode (505) to a drain electrode (506), a second layer (513) configured to control the conductance of the first layer (512) using an electric field formed between the first (512) and second layers (513) and a third layer (514) positioned between the first and second layers to prevent a flow of charge carriers therebetween to enable formation of the electric field, wherein the second layer (513) is configured to exhibit a charge distribution on interaction with the fluid, the charge distribution giving rise to the electric field between the first (512) and second (513) layers, and wherein the second layer (513) is configured such that the charge dis-
(Continued)

tribution and electric field strength are dependent upon the relative vapor pressure of the fluid in the environment (516), thereby allowing the relative vapor pressure to be derived from a measurement of the conductance of the first layer (512).

20 Claims, 5 Drawing Sheets

(51) Int. Cl.
*G01L 9/00* (2006.01)
*G01N 27/02* (2006.01)

(56) References Cited

U.S. PATENT DOCUMENTS

| | | | |
|---|---|---|---|
| 9,080,928 | B2 | 7/2015 | Borini et al. |
| 9,318,591 | B2* | 4/2016 | Geim ............... H01L 29/775 |
| 9,618,474 | B2* | 4/2017 | van Rooyen ........ G01N 27/414 |
| 2006/0263225 | A1 | 11/2006 | Tzong-Ru et al. |
| 2012/0058350 | A1 | 3/2012 | Long et al. |
| 2013/0018599 | A1 | 1/2013 | Peng |
| 2013/0037780 | A1* | 2/2013 | Kivioja ............... H01L 29/84 257/26 |
| 2013/0056839 | A1 | 3/2013 | Holm-Kennedy |
| 2013/0203198 | A1 | 8/2013 | Min et al. |
| 2014/0349211 | A1 | 11/2014 | Wei et al. |

FOREIGN PATENT DOCUMENTS

| | | |
|---|---|---|
| EP | 2629356 A1 | 8/2013 |
| GB | 2145280 | 3/1985 |
| GB | 2145282 | 3/1985 |
| WO | 2008039165 | 4/2008 |
| WO | 2012/033869 A1 | 3/2012 |
| WO | 2012/043912 A1 | 4/2012 |

OTHER PUBLICATIONS

Schedin et al., "Detection of Individual Gas Molecules adsorbed on Graphene", Nature Materials, vol. 6, Sep. 2007, pp. 652-655.
Yao et al., "Electric Current Induced Reduction of Graphene Oxide and Its Application as Gap Electrodes in Organic photoswitching Devices", Advance Materials, 2010, pp. 5008-5012.
Nair et al., "Unimpeded Permeation of WaterThrough Helium-leak-Tight Graphene-Based Membranes", Science, vol. 335, Jan. 27, 2012, pp. 442-444.
Dimiev et al., "Graphene Oxide. Origin of Acidity, Its Instability in Water, and a New Dynamic Structural Model", ACSNano, vol. 7, No. 1, 2013, pp. 576-588.
"Graphene Oxide", Graphene square, Retrieved on Mar. 6, 2017, Webpage available at : http://www.graphenesq.com/products/product_detail.asp?idx=51&p_cate1=630&smenu=3.
Yao et al., "The Effect of Ambient Humidity on the Electrical Properties of Graphene Oxide Films", Nanoscale Research Letters, 2012, pp. 1-7.
Zhao et al., "Humidity Sensing Properties of the Sensor Based on Graphene Oxide Films With Different Dispersion Concentrations", IEEE Sensors, Oct. 28-31, 2011, 4 Pages.
"Graphene the Wonder woman", Science Articles & Inventions Online, Retrieved on Mar. 6, 2017, Webpage available at : http://sciencearticlesonline.com/2012/01/30/is-graphene-the-material-of-the-century-what-cant-it-do-see-here/.
Lee et al., "Cut and stick rubbery ion gels as high capacitance gate dielectrics", Adv Mater, vol. 24, Issue 32, Aug. 22, 2012, pp. 4457-4462.
Sagar et al., "Polymer-electrolyte Gated Graphene Transistors for Analog and Digital Phase Detection", Applied Physics Letters, vol. 99, No. 4, 2011, 4 pages.
Vasu et al., "Probing Top-gated Field Effect Transistor of Reduced Graphene Oxide Monolayer Made by Dielectrophoresis", Solid State Communications, vol. 150, No. 29-30, Aug. 2010, pp. 1-12.
Sagar, "Graphene-based Field-effect Transistors", Thesis, 2011, 113 pages.
Chakraborty et al., "The Formation of a P-n Junction in a Polymer Electrolyte Top-gated Bilayer Graphene Transistor", Nanotechnology, Sep. 5, 2009, 16 pages.
Sharma et al., "Graphene Based Field Effect Transistors: Efforts Made Towards Flexible Electronics", Solid-State Electronics, Nov. 2013, pp. 177-188.
Extended European Search Report received for corresponding European Patent Application No. 14825934.4, dated Mar. 3, 2017, 8 pages.
Jung et al., "Effect of Water Vapor on Electrical Properties of Individual Reduced Graphene Oxide Sheets", The Journal of Physical Chemistry, 2008, pp. 20264-20268.
Basu et al., "Recent Developments on Graphene and Graphene Oxide Based Solid State Gas Sensors", Sensors and Actuators B: Chemical, vol. 173, Oct. 2012, pp. 1-21.
International Search Report and Written Opinion received for corresponding Patent Cooperation Treaty Application No. PCT/FI2014/050513, dated Oct. 10, 2014, 17 pages.
Search Report received for corresponding GB Application No. 1312658.6, dated Nov. 20, 2013, 3 pages.

\* cited by examiner

ENVIRONMENTAL SENSOR AND A METHOD FOR DETERMINING RELATIVE VAPOUR PRESSURE

RELATED APPLICATION

This application was originally filed as PCT Application No. PCT/FI2014/050513 filed Jun. 25, 2014 which claims priority benefit from GB Patent Application No. 1312658.6, filed Jul. 16, 2013.

TECHNICAL FIELD

The present disclosure relates to the field of environmental sensors, associated methods and apparatus, and in particular concerns an apparatus for use in determining the relative vapour pressure of a fluid in an environment in which the apparatus is located. Certain disclosed example aspects/embodiments relate to portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Graphene oxide has recently been considered as a novel material for use in temperature and humidity sensors. The use of graphene oxide as the sensing material enables transparent, flexible sensors to be produced at low cost with improved sensitivity when compared to existing sensors. Such sensors, however, have been found to suffer from the following drawbacks:

(i) Structural degradation—it is known that irreversible modification of graphene oxide occurs during exposure to water (both liquid and vapour) and is thought to be accelerated when there is current flow through the graphene oxide layer.

(ii) Low conductivity—graphene oxide is an insulator and graphene oxide layers of <50 nm in thickness (required for transparency and speed) have sheet resistances of >G$\Omega$/sq. For typical interdigitated electrode designs, especially those using printed electrodes, this constrains the footprint of the sensor to be several tens of mm$^2$. In some circumstances it may be desirable to shrink this sensor layout size.

(iii) AC operation—it has been observed that the operation of graphene oxide sensors under a DC bias results in the build up of an open circuit voltage across the graphene oxide sensing layer and instability in the DC conductance measurement. This has led to the graphene oxide sensors being measured using either AC or pulsed excitation. In some circumstances DC operation may be desirable.

(iv) Sensitivity—although graphene oxide is highly sensitive to relative humidity, a trade-off exists between sensitivity and thickness (which affects transparency and speed).

One or more aspects/embodiments of the present disclosure may or may not address one or more of these issues.

The listing or discussion of a prior-published document or any background in this specification should not necessarily be taken as an acknowledgement that the document or background is part of the state of the art or is common general knowledge.

SUMMARY

According to a first aspect, there is provided an apparatus for use in determining the relative vapour pressure of a fluid in an environment in which the apparatus is located, the apparatus comprising:
 a first layer configured to enable a flow of charge carriers from a source electrode to a drain electrode;
 a second layer configured to control the conductance of the first layer using an electric field formed between the first and second layers; and
 a third layer positioned between the first and second layers to prevent a flow of charge carriers therebetween to enable formation of the electric field,
 wherein the second layer is configured to exhibit a charge distribution on interaction with the fluid, the charge distribution giving rise to the electric field between the first and second layers, and wherein the second layer is configured such that the charge distribution and electric field strength are dependent upon the relative vapour pressure of the fluid in the environment, thereby allowing the relative vapour pressure to be derived from a measurement of the conductance of the first layer.

The term "relative vapour pressure" as used throughout the specification may be taken to mean the ratio between the partial vapour pressure of a fluid and its saturation vapour pressure at a given temperature. The fluid may comprise one or more of a liquid and a gas. The fluid may comprise water. The relative vapour pressure of the fluid may provide an indication of the relative humidity of the environment.

The first layer may comprise graphene. The second layer may comprise graphene oxide. The third layer may comprise one or more of boron nitride, aluminum oxide, hafnium oxide, silicon dioxide and parylene. One or more of the first, second and third layers may have a thickness of one atomic layer.

The second layer may comprise a first material having one or more functional groups configured to release charged particles on interaction with the fluid to produce the charge distribution. The second layer may comprise a second material also having one or more functional groups configured to release charged particles on interaction with the fluid to produce the charge distribution. The first material may be configured to form a junction with the second material. The first material may have a higher concentration of charge-releasing functional groups than the second material such that a concentration gradient of charged particles is produced at the junction on exposure of the second layer to the fluid.

The charged particles may be protons. The charge-releasing functional groups may comprise one or more of a carboxyl, hydroxyl and epoxy group. The first material may comprise graphene oxide. The graphene oxide may comprise a plurality of fully or partially oxidised graphene flakes.

The apparatus may comprise a protective layer configured to prevent damage to one or more of the first, second and third layers without preventing the relative vapour pressure of the fluid in the environment from being determined. The protective layer may comprise a fluid-permeable material such as a block co-polymer or a non-absorbing fabric layer.

The first layer may be patterned to form a channel between the source and drain electrodes. The apparatus may comprise the source and drain electrodes. The apparatus may comprise a back electrode configured to influence the charge distribution within the second layer.

The apparatus may comprise means for measuring/calculating the conductance of the first layer. The apparatus may comprise means for deriving the relative vapour pressure of the fluid in the environment from a measurement/calculation of the conductance of the first layer.

The apparatus may be one or more of an electronic device, a portable electronic device, a portable telecommunications device, a sensor and a module for any of the aforementioned devices.

According to a further aspect, there is provided a method of using an apparatus in determining the relative vapour pressure of a fluid in an environment in which the apparatus is located, the apparatus comprising:
a first layer configured to enable a flow of charge carriers from a source electrode to a drain electrode;
a second layer configured to control the conductance of the first layer using an electric field formed between the first and second layers; and
a third layer positioned between the first and second layers to prevent a flow of charge carriers therebetween to enable formation of the electric field,
wherein the second layer is configured to exhibit a charge distribution on interaction with the fluid, the charge distribution giving rise to the electric field between the first and second layers, and wherein the second layer is configured such that the charge distribution and electric field strength are dependent upon the relative vapour pressure of the fluid in the environment, thereby allowing the relative vapour pressure to be derived from a measurement of the conductance of the first layer, the method comprising:
measuring/calculating the conductance of the first layer; and
deriving the relative vapour pressure of the fluid in the environment from the measured/calculated conductance of the first layer.

According to a further aspect, there is provided a method of making an apparatus for use in determining the relative vapour pressure of a fluid in an environment in which the apparatus is located, the method comprising:
forming first, second and third layers of the apparatus,
the first layer configured to enable a flow of charge carriers from a source electrode to a drain electrode;
the second layer configured to control the conductance of the first layer using an electric field formed between the first and second layers; and
the third layer positioned between the first and second layers to prevent a flow of charge carriers therebetween to enable formation of the electric field,
wherein the second layer is configured to exhibit a charge distribution on interaction with the fluid, the charge distribution giving rise to the electric field between the first and second layers, and wherein the second layer is configured such that the charge distribution and electric field strength are dependent upon the relative vapour pressure of the fluid in the environment, thereby allowing the relative vapour pressure to be derived from a measurement of the conductance of the first layer.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

DESCRIPTION OF SPECIFIC ASPECTS/EMBODIMENTS

Figure 1A:
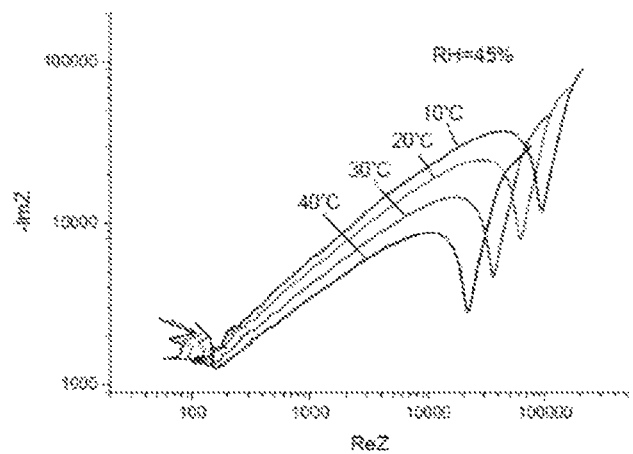
FIG. 1a shows impedance spectra (frequency range 40 Hz-110 MHz) of graphene oxide as a function of temperature.
Figure 1B:
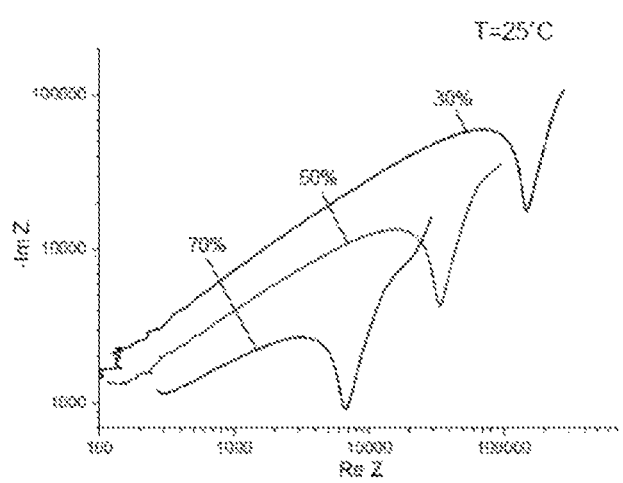
FIG. 1b shows impedance spectra (frequency range 40 Hz-110 MHz) of graphene oxide as a function of relative humidity.

The impedance of graphene oxide has been found to be exponentially dependent upon the temperature and relative humidity of the environment in which it is located. This is illustrated in FIGS. 1a and 1b which show complex impedance spectra of graphene oxide as a function of temperature (at a relative humidity of 45%) and relative humidity (at a temperature of 25° C.), respectively.

Figure 2:
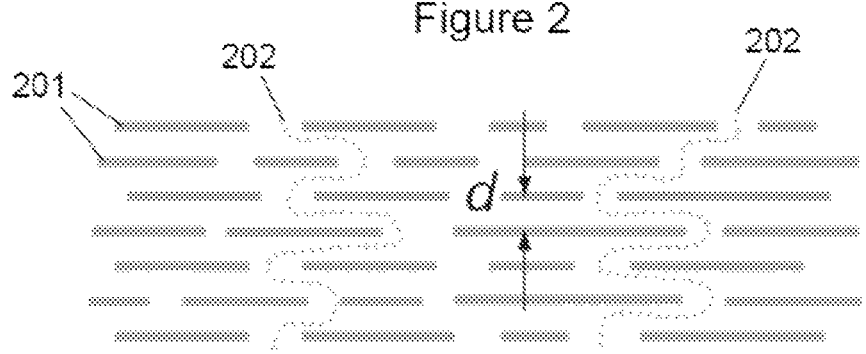
FIG. 2 shows water evaporation through a pseudo two-dimensional stack of graphene oxide platelets.

The temperature and humidity dependence is not fully understood, but may relate to the layered structure of the material. As shown in FIG. 2, graphene oxide comprises a stack of pseudo two-dimensional platelets 201 (with interstitial spacing "d") which allow the permeation of water 202 through the material. The permeation rate depends on both the temperature and relative humidity of the environment.

Figure 3:
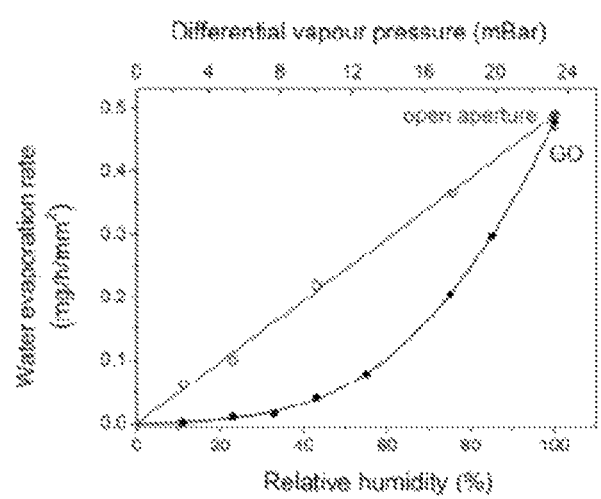
FIG. 3 shows the water permeation rate through an open aperture with and without a graphene oxide membrane as a function of relative humidity.

FIG. 3 shows the rate of water evaporation through an open aperture and the same aperture covered with a 0.5 μm thick graphene oxide membrane. At 100% relative humidity, the water penetrates through the graphene oxide as though the membrane wasn't there. One possible explanation for this behaviour is that the relative humidity (and also the temperature) of the surrounding environment affect the interstitial spacing of the graphene oxide platelets, which in turn dictates the amount of water that can be absorbed by the material. When water fills the space between the platelets, the thickness of the material increases and charge transfer occurs between the water molecules and the graphene oxide resulting in the change in impedance.

As mentioned in the background section, existing graphene oxide-based temperature and humidity sensors have been found to suffer from structural degradation, low conductivity, DC instability and sensitivity trade-off. There will now be described an apparatus and associated methods that may or may not provide a solution to one or more of these issues.

Figure 4:
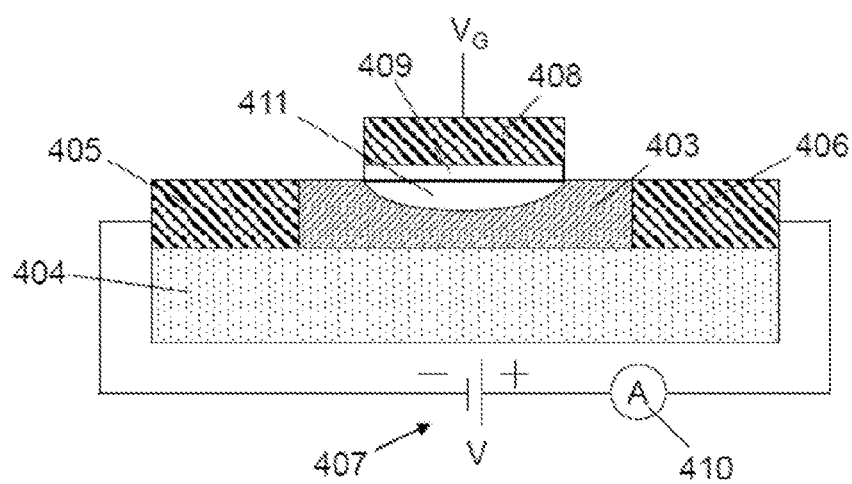
FIG. 4 shows a conventional field effect transistor.

One or more disclosed embodiments of the present apparatus comprise a field effect transistor (FET) for use in determining the relative vapour pressure of a fluid in an environment in which the apparatus is located. An FET is a type of transistor in which an electrical current is carried along a conduction channel, the conductance of which can be controlled by a transverse electric field. In a conventional FET setup (as illustrated in FIG. 4), a semiconductor 403 such as p-type silicon is supported on a substrate 404 and connected to metal source 405 and drain 406 electrodes. A current is injected and collected via the source 405 and drain 406 electrodes, respectively, by applying a potential difference (V) 407 across the semiconductor 403. The conductance of the semiconductor 403 between the source 405 and drain 406 electrodes is switched on and off by a third electrode (the gate electrode 408) capacitively coupled through a thin dielectric layer 409. The conductance may be determined by measuring the current through the semiconductor 403 (using an ammeter 410, for example) and dividing by the potential difference (V) 407. With p-type silicon (or another p-type semiconductor), application of a positive gate voltage ($V_G$) depletes the charge carriers (creating a depletion region 411 in the semiconductor 403) and reduces the conductance, whilst applying a negative gate voltage ($V_G$) leads to an accumulation of charge carriers (creating a conductive region) and an increase in conductance.

Figure 5:
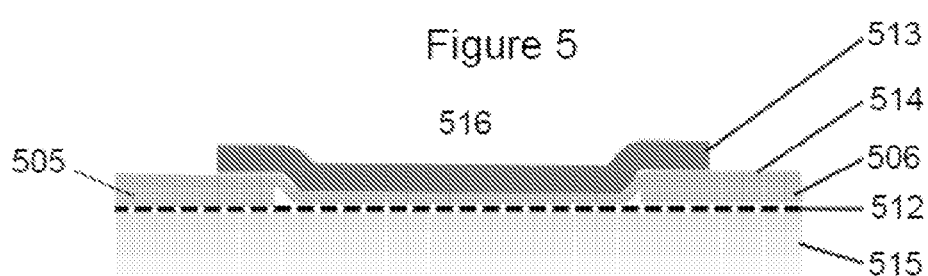
FIG. 5 shows an apparatus according to one embodiment of the present disclosure.

As shown in FIG. 5, one embodiment of the present apparatus comprises a first layer 512 configured to enable a flow of charge carriers from a source electrode 505 to a drain electrode 506, a second layer 513 configured to control the conductance of the first layer 512 using an electric field formed between the first 512 and second 513 layers, and a third layer 514 positioned between the first 512 and second 513 layers to prevent a flow of charge carriers therebetween to enable formation of the electric field. Typically, the first 512, second 513 and third 514 layers would be formed on top of a supporting substrate 515 as shown. The second layer 513 is configured to exhibit a charge distribution on interaction with fluid in the surrounding environment 516, the charge distribution giving rise to the electric field between the first 512 and second 513 layers. The second layer 513 is further configured such that the charge distribution and electric field strength are dependent upon the relative vapour pressure of the fluid in the environment 516, thereby allowing the relative vapour pressure to be derived from a measurement of the conductance of the first layer 512.

Since the electrical current is passed through the first layer 512 rather than the second (i.e. fluid-sensitive) layer 513 during operation, graphene oxide may be used in the second layer 513 without suffering from the above-mentioned structural degradation, low conductivity and DC instability issues. Furthermore, any reduction in sensitivity caused by the low thickness of the graphene oxide can be compensated for by using an ultrasensitive material (e.g. graphene) in the first layer 512.

In the embodiment shown in FIG. 5, the second layer 513 comprises a single material having one or more functional groups configured to release charged particles on interaction with the fluid to produce the charge distribution. For example, the material may comprise graphene oxide having one or more carboxyl, hydroxyl and/or epoxy groups. When such a material interacts with water (e.g. when the apparatus is being used to determine the relative humidity of the surrounding environment 516), protonation occurs at the surface of the material creating protons ($H^+$) and negatively charged functional groups (e.g. $COO^-$). The protons and negatively charged functional groups form electric dipoles in the material which influence the conductance of the first layer 512 via electric fields. As the relative vapour pressure of the fluid increases, an increased concentration of electric dipoles is produced resulting in a corresponding change in the conductance of the first layer 512.

The sensitivity of the apparatus can be increased in several different ways. One method is to use a material in the first layer 512 whose conductance is highly sensitive to local changes in electric field strength. The sensitivity can be increased further by patterning the first layer 512 to form a channel between the source 505 and drain 506 electrodes and/or by minimising the thickness of the first 512 and third 514 layers. Ideally the first 512 and third 514 layers should have a thickness of one atomic layer, which is achievable with pseudo-two-dimensional crystal materials. In this respect, graphene is a suitable candidate for the first layer 512, whilst dielectric materials such as boron nitride, aluminum oxide, hafnium oxide, silicon dioxide or parylene may be used for the third layer 514.

Figure 6:
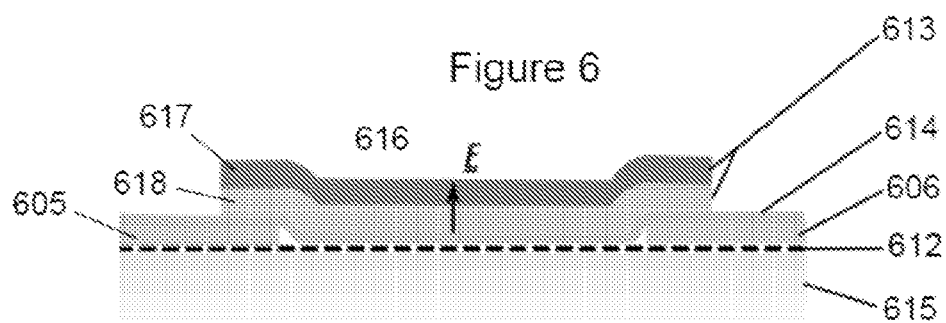
FIG. 6 shows an apparatus according to another embodiment of the present disclosure.

FIG. 6 shows another embodiment of the present apparatus. In this example, the second layer 617 comprises a junction formed by first 617 and second 618 materials each having one or more functional groups configured to release charged particles on interaction with the fluid to produce the charge distribution. The first material 617 has a higher concentration of charge-releasing functional groups than the second material 618. In this way, a concentration gradient of charged particles is produced at the junction on exposure of the second layer 613 to the fluid which results in a more pronounced electric field between the first 612 and second 613 layers.

Figure 7:
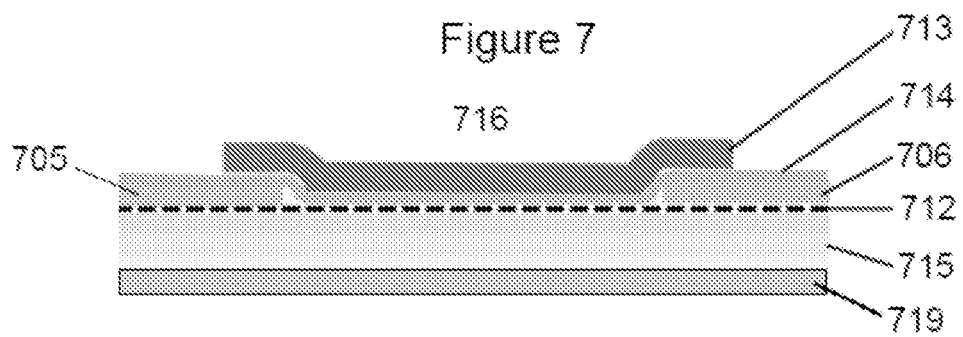
FIG. 7 shows an apparatus according to another embodiment of the present disclosure.

In the embodiments shown in FIGS. 5 and 6, the apparatus comprises two electrodes only (i.e. the source 505, 605 and drain 506, 606 electrodes). In the embodiment shown in FIG. 7, however, the apparatus comprises an additional back electrode 719 configured to influence the charge distribution within the second layer 713. For example, the back electrode 719 may be used to promote the migration of charged particles (such as protons) towards or away from the interface between the first 712 and second 713 layers to further increase the sensitivity of the apparatus.

Figure 8:
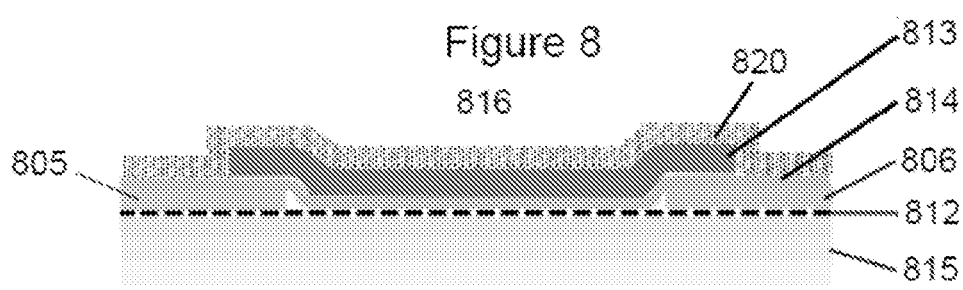
FIG. 8 shows an apparatus according to another embodiment of the present disclosure.

FIG. 8 shows another embodiment of the present apparatus. In this example, the apparatus comprises a protective layer 820 configured to prevent damage to the first 812, second 813 and third 814 layers without preventing the relative vapour pressure of the fluid in the environment from being determined. To achieve this functionality, the protective layer 820 comprises a fluid-permeable material such as a block co-polymer or a non-absorbing fabric layer.

Figure 9:
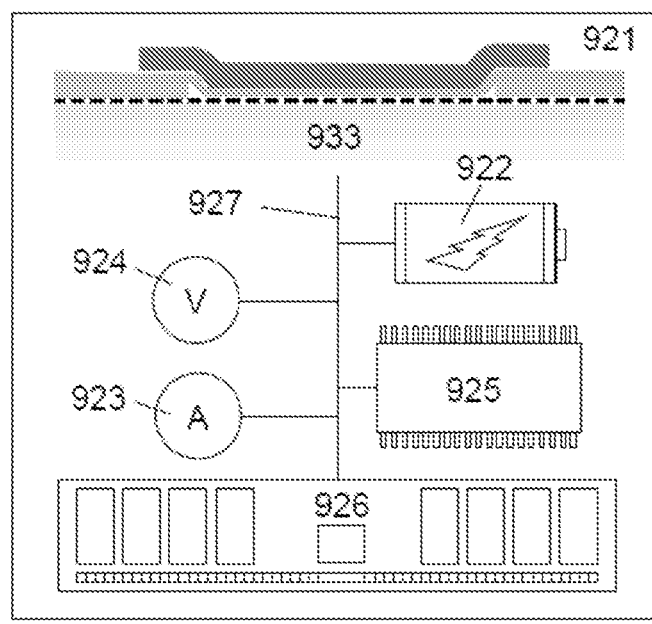
FIG. 9 shows an apparatus according to another embodiment of the present disclosure.

FIG. 9 shows a further embodiment of the apparatus described herein. The apparatus may be one or more of an electronic device, a portable electronic device, a portable telecommunications device, a sensor and a module for one or more of the same. In the example shown, the apparatus is a sensor 921 comprising the first, second and third layers, source and drain electrodes (i.e. the components 933 described previously), a power source 922, an ammeter 923, a voltmeter 924, a processor 925 and a storage medium 926, which are electrically connected to one another by a data bus 927.

The power source 922 is configured to apply a voltage between the source and drain electrodes, the voltmeter 924 is configured to measure the applied voltage, and the ammeter 923 is configured to measure the resulting current flowing through the first layer.

The processor 925 is configured for general operation of the apparatus 921 by providing signaling to, and receiving signaling from, the other components to manage their operation. In addition, the processor 925 is configured to receive the voltage and current measurements from the voltmeter 924 and ammeter 923, respectively, and calculate the conductance (G=I/V) of the first layer to derive the relative vapour pressure of the fluid in the environment. In another embodiment, the apparatus 921 may comprise a conductance meter instead of (or in addition to) the voltmeter 924 and ammeter 923 in order to measure the conductance of the first layer directly, and the processor 925 may be configured to receive the conductance measurement from the conductance meter to derive the relative vapour pressure of the fluid in the environment.

The storage medium 926 is configured to store computer code configured to perform, control or enable operation of the apparatus 921. The storage medium 926 may also be configured to store settings for the other components. The processor 925 may access the storage medium 926 to retrieve the component settings in order to manage the operation of the other components. The storage medium 926 may also be configured to store calibration data (e.g. predetermined measurements of relative vapour pressure versus conductance) for use by the processor 925 in deriving the relative vapour pressure of the fluid in the environment.

The processor 925 may be a microprocessor, including an Application Specific Integrated Circuit (ASIC). The storage medium 926 may be a temporary storage medium such as a volatile random access memory. On the other hand, the storage medium 926 may be a permanent storage medium such as a hard disk drive, a flash memory, or a non-volatile random access memory.

Figure 10:
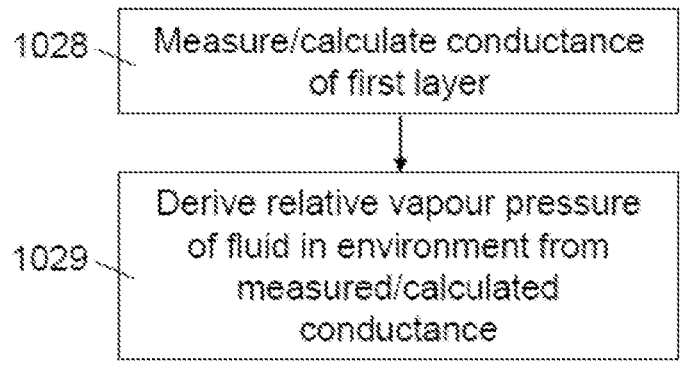
FIG. 10 shows the main steps of a method of determining the relative vapour pressure of an environment using the apparatus described herein.

The main steps 1028-1029 of a method of using the apparatus in determining the relative vapour pressure of a fluid in the environment are shown schematically in FIG. 10. Similarly, the main steps 1130-1131 of a method of making the apparatus are shown schematically in FIG. 11.

A number of different fabrication processes may be used to form the above-mentioned apparatus. According to one example, a first layer material (e.g. graphene) is deposited on a supporting substrate (e.g. polyethylene terephthalate, polyethylene naphthalate, glass, silicon, silicon dioxide, polydimethylsiloxane or polyurethane). Electrical contacts are then formed on the first layer material (e.g. using inkjet, screen, stencil or flexographic printing; evaporation or sputtering) to produce the source and drain electrodes. Suitable electrode materials include metals such as gold, silver and copper; printed metals such as silver nanoparticles; multi-layer graphene; graphene ink or reduced graphene oxide. A conductive channel is then defined in the first layer using a subtractive process such as oxygen plasma etching or laser micromachining, before a third layer material (e.g. 2D boron nitride, aluminum oxide, hafnium oxide, silicon dioxide or parylene) is deposited thereon. The third layer material may be deposited using Langmuir-Blodgett, spray coating, atomic layer deposition, evaporation, sputtering or printing. A second layer material is then deposited on top of the third layer material followed by an optional protective layer.

When graphene oxide is used for the second layer, it may comprise a plurality of fully or partially oxidised graphene flakes with various functional groups attached thereto. Furthermore, the size and number of the oxidised graphene layers may vary. Graphene oxide solution (concentration: 1 g/L; composition: carbon (79%), oxygen (20%); flake size: 0.5-0.7 μm; and thickness: 1 atomic layer (at least 60%)) can be obtained from Graphene Square, Inc and deposited using spray coating, drop casting, spin coating or inkjet printing.

Figure 12:
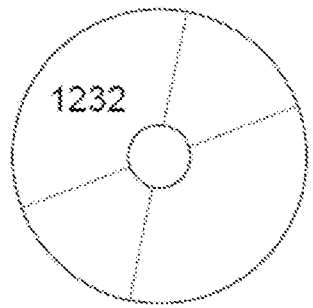
FIG. 12 shows a computer-readable medium comprising a computer program configured to perform, control or enable one or more of the method steps of FIG. 10 or 11.

FIG. 12 illustrates schematically a computer/processor readable medium 1232 providing a computer program according to one embodiment. In this example, the computer/processor readable medium 1232 is a disc such as a digital versatile disc (DVD) or a compact disc (CD). In other embodiments, the computer/processor readable medium 1232 may be any medium that has been programmed in such a way as to carry out an inventive function. The computer/processor readable medium 1232 may be a removable memory device such as a memory stick or memory card (SD, mini SD, micro SD or nano SD).

Figure 11:
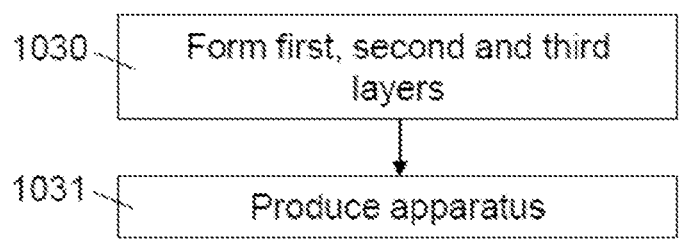
FIG. 11 shows the main steps of a method of making the apparatus described herein.

The computer program may comprise computer code configured to perform, control or enable one or more of the method steps 1028-1029, 1130-1131 of FIG. 10 or 11. In particular, the computer program may be configured to measure/calculate the conductance of the first layer, and determine the relative vapour pressure of the fluid in the environment based on the measured/calculated conductance of the first layer. Additionally or alternatively, the computer program may be configured to control the above-mentioned fabrication processes to form the first, second and third layers of the apparatus.

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signaling" may refer to one or more signals transmitted as a series of transmitted and/or received signals. The series of signals may comprise one, two, three, four or even more individual signal components or distinct signals to make up said signaling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus for determining a relative vapour pressure of a fluid in an environment in which the apparatus is located, the apparatus comprising:
  a source electrode formed on a first layer;
  a drain electrode formed on the first layer;
  the first layer, patterned to form a channel between the source and drain electrode, and configured to enable a flow of charge carriers from the source electrode to the drain electrode;
  a second layer configured as a gate electrode, open to at least the fluid in the environment, and comprising one or more materials having one or more functional groups configured to release charged particles on interaction with the fluid to produce a charge distribution, wherein the charge distribution gives rise to an electric field between the first and second layers; and
  a third layer positioned between the first and second layers and configured to prevent a flow of charge carriers therebetween to enable formation of the electric field, the third layer covering exposed surfaces of the channel of the first layer and the source and drain electrodes;
  wherein the second layer is configured such that the charge distribution and electric field strength are dependent upon the relative vapour pressure of the fluid in the environment, thereby allowing the relative vapour pressure to be derived from a measurement of the conductance of the first layer.

2. The apparatus of claim 1, wherein the first layer comprises graphene.

3. The apparatus of claim 1, wherein the one or more materials of the second layer comprise graphene oxide.

4. The apparatus of claim 1, wherein the one or more materials of the second layer comprise a first material having one or more functional groups configured to release charged particles on interaction with the fluid to produce the charge distribution.

5. The apparatus of claim 4, wherein the one or more materials of the second layer comprise a second material also having one or more functional groups configured to release charged particles on interaction with the fluid to produce the charge distribution, wherein the second material is different from the first material.

6. The apparatus of claim 5, wherein the first material contacts the second material, wherein the first material and the second material have a junction at their contact, and wherein the first material has a higher concentration of charge-releasing functional groups than the second material such that a concentration gradient of charged particles is produced at the junction on exposure of the second layer to the fluid.

7. The apparatus of claim 4, wherein the charged particles are protons.

8. The apparatus of claim 4, wherein the charge-releasing functional groups comprise one or more of a carboxyl, hydroxyl and epoxy group.

9. The apparatus of claim 4, wherein the first material comprises graphene oxide.

10. The apparatus of claim 9, wherein the graphene oxide comprises a plurality of fully or partially oxidised graphene flakes.

11. The apparatus of claim 9, wherein the third layer comprises one or more of boron nitride, aluminium oxide, hafnium oxide, silicon dioxide and parylene.

12. The apparatus of claim 9, wherein one or more of the first, second and third layers have a thickness of one atomic layer.

13. The apparatus of claim 9, wherein the apparatus comprises a protective layer over exposed surfaces of at least the second layer, and wherein the protective layer comprises a fluid-permeable material to enable the second layer to be open to the fluid.

14. The apparatus of claim 9, wherein the apparatus comprises a back electrode configured to influence the charge distribution within the second layer.

15. The apparatus of claim 9, wherein the fluid comprises water, and wherein the relative vapour pressure of the fluid provides an indication of the relative humidity of the environment.

16. The apparatus of claim 9, wherein the apparatus is one or more of an electronic device, a portable electronic device, a portable telecommunications device, a sensor and a module for any of the aforementioned devices.

17. The apparatus of claim 1, wherein the third layer comprises one or more dielectric materials.

18. The apparatus of claim 17, wherein the first layer comprises graphene and the second layer comprises graphene oxide.

19. A method of using an apparatus in determining the relative vapour pressure of a fluid in an environment in which the apparatus is located, the method comprising:

causing in a sensor of the apparatus a potential difference between a source electrode and a drain electrode in a first layer of the sensor, wherein the first layer is patterned to form a channel between the source and drain electrode and enable a flow of charge carriers at a first layer from the source electrode to the drain electrode in response to the potential difference;

wherein the sensor comprises a second layer configured as a gate electrode, open to at least the fluid in the environment, and comprising one or more materials having one or more functional groups configured to release charged particles on interaction with the fluid to produce a charge distribution, wherein the charge distribution gives rise to an electric field between the first and second layers;

wherein the sensor comprises a third layer positioned between the first and second layers and preventing a flow of prevent a flow of charge carriers between the first and second layers to enable formation of the electric field, the third layer covering exposed surfaces of the channel of the first layer and the source and drain electrodes;

wherein the second layer is configured such that the charge distribution and electric field strength are dependent upon the relative vapour pressure of the fluid in the environment, thereby allowing the relative vapour pressure to be derived from a measurement of a conductance of the first layer;

causing the conductance of the first layer to be measured by the apparatus; and causing the apparatus to derive the relative vapour pressure of the fluid in the environment from the measured conductance of the first layer.

20. A computer program comprising a non-transitory computer-readable medium containing computer code, the computer code configured to cause an apparatus to perform a method comprising:

causing in a sensor of the apparatus a potential difference between a source electrode and a drain electrode in a first layer of the sensor, wherein the first layer is patterned to form a channel between the source and drain electrode and enables a flow of charge carriers at a first layer from the source electrode to the drain electrode in response to the potential difference;

wherein the sensor comprises a second layer configured as a gate electrode, open to at least the fluid in the environment, and comprising one or more materials having one or more functional groups configured to release charged particles on interaction with the fluid to produce a charge distribution, wherein the charge distribution gives rise to an electric field between the first and second layers;

wherein the sensor comprises a third layer positioned between the first and second layers and preventing a flow of prevent a flow of charge carriers between the first and second layers to enable formation of the electric field, the third layer covering exposed surfaces of the channel of the first layer and the source and drain electrodes;

wherein the second layer is configured such that the charge distribution and electric field strength are dependent upon the relative vapour pressure of the fluid in the environment, thereby allowing the relative vapour pressure to be derived from a measurement of a conductance of the first layer;

causing the conductance of the first layer to be measured by the apparatus; and causing the apparatus to derive the relative vapour pressure of the fluid in the environment from the measured conductance of the first layer.

* * * * *